United States Patent
Park et al.

(10) Patent No.: US 10,337,035 B2
(45) Date of Patent: Jul. 2, 2019

(54) METHOD FOR PREPARING ORGANIC ACID BY FED-BATCH-FEEDING CARBON SOURCE SUBSTRATE AND BASE

(71) Applicants: SK Innovation Co., Ltd., Seoul (KR); SK Energy Co., Ltd., Seoul (KR)

(72) Inventors: Jae Yeon Park, Seoul (KR); Sin Young Kang, Daejeon (KR); Woo Chan Park, Daejeon (KR); Min Su Koo, Daejeon (KR); In Ho Cho, Seoul (KR); Joong Min Park, Seoul (KR); Seung Yeop Lee, Daejeon (KR); Dong Hyun Kim, Daejeon (KR)

(73) Assignees: SK INNOVATION CO., LTD., Seoul (KR); SK ENERGY CO., LTD., Seoul (KR)

( * ) Notice: Subject to any disclaimer, the term of this patent is extended or adjusted under 35 U.S.C. 154(b) by 0 days.

(21) Appl. No.: 14/402,980

(22) PCT Filed: May 21, 2013

(86) PCT No.: PCT/KR2013/004439
§ 371 (c)(1),
(2) Date: Nov. 21, 2014

(87) PCT Pub. No.: WO2013/176460
PCT Pub. Date: Nov. 28, 2013

(65) Prior Publication Data
US 2015/0140615 A1    May 21, 2015

(30) Foreign Application Priority Data

May 23, 2012 (KR) .................. 10-2012-0054740

(51) Int. Cl.
*C12P 7/52* (2006.01)
*C12P 7/40* (2006.01)
(Continued)

(52) U.S. Cl.
CPC .............. *C12P 7/52* (2013.01); *C12P 7/40* (2013.01); *C12P 7/46* (2013.01); *C12P 7/54* (2013.01); *C12P 7/56* (2013.01)

(58) Field of Classification Search
None
See application file for complete search history.

(56) References Cited

U.S. PATENT DOCUMENTS 5,503,750 A    4/1996    Russo et al.
5,766,439 A    6/1998    Eyal et al.
(Continued)

FOREIGN PATENT DOCUMENTS

JP    49-34835       2/1969
JP    2009-254323 A  4/2006
(Continued)

OTHER PUBLICATIONS

Rughoonundun et al., Bioresource Technology 112: 91-97 (2012).*
(Continued)

*Primary Examiner* — Erin M. Bowers
(74) *Attorney, Agent, or Firm* — Abelman, Frayne & Schwab

(57) ABSTRACT

The present invention provides a fed-batch culture method comprising a step of fed-batch-feeding a carbon source base and a base in such a manner that the pH level can be maintained at a level suitable for the growth of microorganisms for fermentation of a carbon source. The present invention also provides a method for preparing organic acids using the fed-batch culture method. The present invention fed-batch-feeds a neutralizing agent such as ammonium bicarbonate, ammonium carbonate or alkali metal-containing weak base, and a carbon source substrate in preparing organic acids by microorganism fermentation. Thus, a pH level suitable for the survival of microorganisms for carbon (Continued)

source fermentation can be maintained, and the speed of injecting the carbon source base which is the source material can be appropriately adjusted. The present invention may improve productivity, yield rate and concentration of organic acids and may automatically inject a base and a carbon source substrate according to a variation in the pH level, thus improving reliability and convenience of a fermentation process operation.

9 Claims, 1 Drawing Sheet

(51) Int. Cl.
    *C12P 7/46*     (2006.01)
    *C12P 7/54*     (2006.01)
    *C12P 7/56*     (2006.01)

(56) References Cited

U.S. PATENT DOCUMENTS

| | | |
|---|---|---|
| 2006/0014260 A1 | 1/2006 | Fan et al. |
| 2011/0177567 A1 | 7/2011 | Bakker et al. |
| 2013/0164801 A1 | 6/2013 | Kang et al. |

FOREIGN PATENT DOCUMENTS

| | | | |
|---|---|---|---|
| JP | 2010-017082 A | | 1/2010 |
| KR | 2010-0074010 A | | 7/2010 |
| KR | 2011-0081518 A | | 7/2011 |
| KR | 20120025998 | * | 3/2012 |
| KR | 20120025998 A | | 3/2012 |
| WO | 2009025547 A1 | | 2/2009 |
| WO | 2009154624 A1 | | 12/2009 |

OTHER PUBLICATIONS

He et al., J. Zhejiang Univ. Sci. 6B(11): 1076-1080 (2005).*
Chen, "Chapter 3: Nitrogen Fixation in the Clostridia", in Klipp et al., Genetics and Regulation of Nitrogen Fixation in Free-Living Bacteria, pp. 53-64, Kluwer, 2004.*
PCT/KR2013/00439, International Search Report and Written Opinion, dated Aug. 27, 2013 (11 pages).
Liu, Juan-Bin et al. "Process of rice straw degradation and dynamic trend of pH by the microbial community MC1", Journal of Environmental Sciences, 2006, vol. 18, No. 6, pp. 1142-1146.
Ohkouchi, Y. et al. "Direct production of l(+)-lactic acid from starch and food wastes using Lactobacillus manihotivorans LMG18011", Bioresource Technology, Sep. 2006, vol. 97, No. 13, pp. 1554-1562.
Japanese Summary of Office Action dated Feb. 28, 2017.
Korean Office Action and Translation of Summary of Office Action dated May 30, 2017.

* cited by examiner

United States Patent US 10,337,035 B2

METHOD FOR PREPARING ORGANIC ACID BY FED-BATCH-FEEDING CARBON SOURCE SUBSTRATE AND BASE

TECHNICAL FIELD

The present invention relates to a method for producing an organic acid by fed-batch culturing. More particularly, the present invention relates to a method for producing an organic acid by feeding a carbon source and a base in a fed-batch manner.

BACKGROUND ART

For use in various foods, food additives, chemical materials, etc., organic acids have been long produced by fermentation. In recent years, organic acids have been evaluated as resources highly available as raw materials for fuels and chemical materials useful in the development of new environmentally friendly renewable energy and chemicals.

Fermentation for the production of organic acids is generally conducted in a batch manner. The production of organic acids by fermentation is disclosed in U.S. Pat. Nos. 5,503,750 and 5,766,439. According to batch fermentation, microorganisms for producing an organic acid of interest are grown in a bioreactor where a limited supply of nutrients for the growth, such as sugars, a nitrogen source, minerals, etc, are fed simultaneously. Since the yield of organic acids from a limited supply of sugars is limited, a high concentration of the sugars is initially employed to give a greater amount of the organic acids in a batch culture. However, a high concentration of sugars acts as a cause of inhibiting the growth of microorganisms to decrease fermentation rate. Fed-batch culture is suggested as an alternative to solve the problem.

Fed-batch culture is an operational technique in biotechnological processes where batch culture is initially conducted at a suitable sugar concentration, and then high concentration sugar is subsequently supplied to maintain low concentration of sugar in the culture medium. In regard to this technique, there are various fed-batch culture methods that are dependent on when, how, and how much to feed sugars. The growth rate of microorganisms and product yield can be affected according to each methods.

Sugar controlling techniques known to date include an manually feeding sugar at a constant rate determined according to the growth pattern analysis of microorganisms, and automatically feeding sugar in response to the information on DO (dissolved oxygen) or pH (hydrogen exponent). When employing the former technique, fed-batch culture may improve in productivity and yield, compared to batch culture, but may be inefficient because sugar cannot be fed accurately in concert with microorganisms growth and sugar consumption. Further, the operator should continually observe the feeding amount of sugar.

As for the latter technique, pH stat or OD stat fed-batch fermentation is widely employed for culturing aerobic microorganisms such as *E. coli* because it causes sugar concentrations in the culture to fluctuate little, and matches the profile of microorganisms growth. Particularly, pH-stat fed-batch culture was developed in consideration of the pH drop phenomenon that occurs as aerobic microorganisms such as *E. coli* metabolizes sugars, and is designed to feed sugar at a concentration that is minimal but not decreases the activity of microorganisms. In the pH-stat fed-batch mode, a desired pH is set, and a small amount of sugar is fed when the pH of the culture exceeds the allowance of the set value. As a small amount of sugar is metabolized, the pH slightly decreases. If the sugar is completely consumed, the pH of the culture again increases, and thus sugar is fed. This cycle is continued until the product is obtained in a desired amount. Upon fermentation for organic acid production, however, the culture does not undergo the sugar consumption-induced slight increase of pH, but constantly decreases in pH with the production of organic acids. Therefore, conventional fed-batch culture, such as pH stat, cannot be applied to fermentation for the production of organic acids.

DISCLOSURE

Technical Problem

Keeping in mind the problem that conventional fed-batch culture is unsuitable for use in fermentation for the production of organic acids as the culture continues to decrease in pH, with the production of organic acids, the present inventors conceived a method for producing an organic acid in which a carbon source substrate (sugar) and a base are fed in a fed-batch mode to establish an optimal condition for the growth of an anaerobic microorganism that produces the organic acid.

An aspect of the present invention pertains to a method for producing an organic acid by feeding a carbon source simply and reliably in a fed-batch manner whereby a high concentration of the organic acid can be obtained with high productivity and yield.

Technical Solution

In accordance with an aspect thereof, the present invention provides a method for producing an organic acid by feeding a mixture of i) a carbon source substrate; and ii) at lease one base selected from among ammonium bicarbonate or an alkali metal-containing weak base (e.g., sodium bicarbonate, potassium bicarbonate, sodium carbonate, potassium carbonate) in a fed-batch manner to a bioreactor containing an organic acid-producing microorganism strain, whereby the culture can be properly adjusted in pH and carbon source substrate concentration at the same time against a change in pH and carbon source substrate (e.g., sugar) concentration as fermentation proceeds.

In another aspect thereof, the present invention provides a method for producing butyric acid by the fed-batch culture method of the present invention.

Advantageous Effects

The method of the present invention is configured to feed a carbon source at a rate depending on the rate at which a base is fed in response to a pH change. In a fermentation system for the production of organic acids, a carbon source is fed, along with a base, in a fed-batch manner to maintain the carbon source at a constant concentration in a culture medium in accordance with the present invention. Compared to a conventional method in which an operator determines the feeding rate of sugar after directly measuring the concentration of the carbon source or the pH of the culture medium or analyzing microorganism growth by hour, hence, the method of the present invention is superior in productivity and yield in addition to being simpler and more reproducible.

According to the method of the present invention, further, fermentation can last until the carbon source is completely exhausted so that a maximum production yield can be obtained, with the concomitant production of by-products such as acetic acid to much less extent Moreover, a need for a medium for seed culture, which is generally expensive, is removed or reduced. Consequently, the method of the present invention provides an economical strategy of reducing the cost of fermentation processes.

MODE FOR INVENTION

Figure 1:
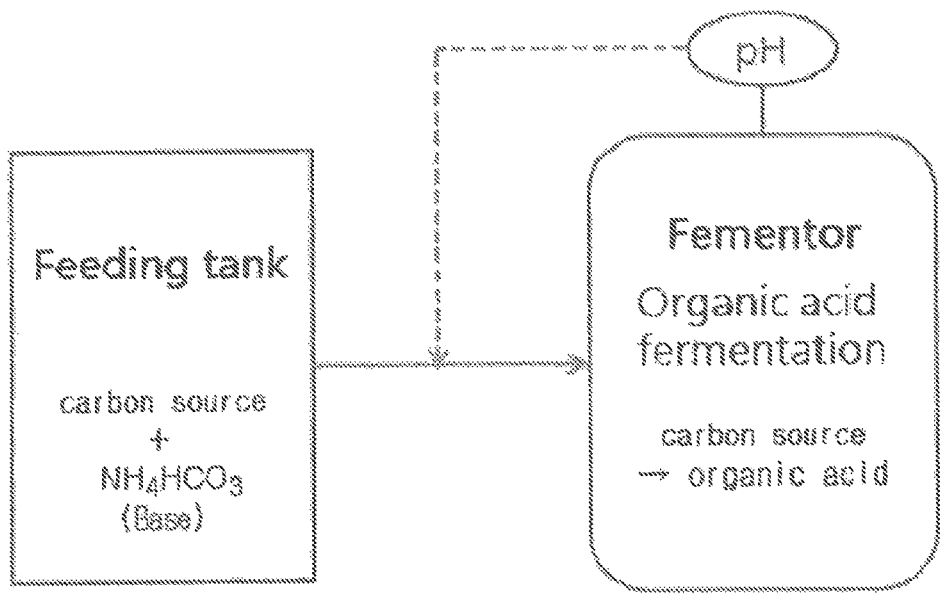
FIG. 1 is a schematic view of a system in which an organic acid is produced by fed-batch culture in accordance with an embodiment of the present invention.

The present invention is based on the fact that there is direct correlation between the consumption of carbon source by microorganisms and the content of produced organic acids (e. g. lowered pH). A culture for producing an organic acid becomes low in the content of a carbon source and in pH as the organic acid is produced. In the present invention, a substrate-base mixture of a carbon source and at least one base selected from among ammonium bicarbonate and an alkali metal-containing weak base is supplied in a fed-batch type to supplement the lowered content of a carbon source and to increase the lowered pH value due to production of the organic acid, thereby improving the productivity of the organic acid.

Strong bases such as NaOH, KOH, and $Ca(OH)_2$ may be employed to neutralize organic acids produced in a culture, but they, inter alia, calcium (Ca)-containing bases, are highly apt to denature and precipitate proteins. Entering a medium, such strong bases denature a nitrogen source to inhibit the utility of the nitrogen source by microorganisms, resulting in a decrease in fermentation efficiency. Hence, a weak base, particularly, ammonium bicarbonate, or an alkali metal-containing weak base such as sodium bicarbonate, potassium bicarbonate, etc., or both are used in neutralizing organic acids in the present invention. Ammonium bicarbonate is advantageous because it can act as a nutrient source of ammonium ions necessary for the growth of microorganisms, as well.

Below, a detailed description will be given of the present invention.

An aspect of the present invention addresses a method for producing an organic acid through fermentation of a carbon source substrate, comprising feeding a substrate-base mixture containing i) a carbon source substrate; and ii) at least one base selected from among ammonium bicarbonate, ammonium carbonate, and an alkali metal-containing base in a fed-batch manner to a bioreactor containing a carbon source substrate and an organic acid-producing strain to maintain pH suitable for growth of microorganisms fermenting the carbon source substrate.

According to one embodiment thereof, the present invention provides a method for producing an organic acid by fed-batch culture, comprising:

preparing a culture medium containing a carbon source substrate, an organic acid-producing strain, and an essential ingredient for growth of the strain (strain growth ingredient);

fermenting the carbon source substrate in an optimal condition established by feeding a substrate-base mixture of a carbon source substrate and at least one base selected from ammonium bicarbonate, ammonium carbonate, and alkali metal-containing weak base in a fed-batch manner to the culture medium to allow the culture medium to have a pH value optimal for growth of the organic acid-producing strain; and recovering the organic acid from the culture medium, the organic acid being produced with the fermentation of the carbon source substrate.

The term "weak base" is meant as a base containing an alkali metal of Group 1 in the Periodic Table, as exemplified by sodium bicarbonate and potassium bicarbonate.

In one embodiment of the present invention, the carbon source substrate may be a sugar that may in the form of monosacharrides, disaccharides, polysaccharides, and a combination thereof. Examples include, but are not limited to, glucose, fructose, sucrose, galactose, mannose, xylose, arabinose, sugar cane, molasses, and starch hydrates.

Content ratios between carbon source substrate and base in the substrate-base mixture to be supplied during fermentation may be adjusted in concert with fermentation characteristics in consideration of the solubility of the base and the production rate of the organic acid. Under the assumption that the carbon source substrate and the base are maintained aseptically, the content ratio between carbon source substrate and base may be adjusted even while the fermentation process is running.

The carbon source substrate fed in the fed-batch manner may be the same or different from the carbon source substrate initially contained in the culture medium the bioreactor.

Within the scope of the ingredient essential for the growth of the microorganism strain, a nitrogen source, a vitamin, an inorganic salt, and/or a carbon source decomposing enzyme such as an invertase in addition to the carbon source substrate may fall. A person of ordinary skill in the art may readily determine ingredients necessary for the growth according to the strain.

Among the range of the organic acid that can be produced in the fed-batch culture method of the present invention are butyric acid, lactic acid, acetic acid, formic acid, citric acid, adipic acid, succinic acid, fumaric acid, malic acid, 3-hydroxypropionic acid, glutamic acid, glutaric acid, glucaric acid, itaconic acid, acrylic acid, and muconic acid, which are known to be useful as biofuels and biochemicals.

So long as it produces an organic acid, any microorganism may be used as the organic acid-producing strain in the present invention. The organic acid-producing strain may be selected from among *Clostridium* spp., *Pseudomonas* spp., *Rhizopus* spp., *Aspergillus* spp., *Corynebacterium* spp., *Actinobacillus* spp., yeast, *Candida* spp., *Pichia* spp., *E. coli*, and lactic acid bacteria. Concrete examples of the organic acid-producing strain include *Clostridium tyrobutyricum, C. butyricum, C. acetobutyricum, Pseudomonas aeruginosa, P. putida, P. fluorescens, Rhizopus arrhizus, R. oryzae, Aspergillus oryzae, Corynebacterium glutamicum*, and *Lactobacillus acidophilus*.

Fermentation conditions proper for individual strains are known in the art.

As used herein, the term "optimal condition" in context with strain growth means an environment, including an anaerobic condition, a temperature range, and a pH range, under which a microorganism strain grows, with the concomitant maximal production of the organic acid. The optimal condition may be changed depending on the strain used. The person having ordinary skill of the art may adjust the environment of the bioreactor into an optimal condition depending on the growth stage of the microorganism strain. For example, the bioreactor may be set to be heated or cooled to a temperature of 20 to 50° C. while the culture medium may have a pH of 4 to 7.

Also, contemplated in one embodiment of the present invention is a method for producing butyric acid by fermenting sugars in the presence of a Clostridium strain, with the supply of sugars and at least one base selected from among sodium bicarbonate and potassium bicarbonate in a fed-batch manner As needed for fermentation, a carbon source substrate, a nitrogen source, vitamins and minerals and/or an enzyme such as invertase may be added to the culture medium.

More particularly, the present invention provides a method for producing butyric acid by fed-batch culturing, comprising:

preparing a culture medium containing a carbon source substrate, a butyric acid-producing microorganism strain, and an essential ingredient for growth of the strain (growth essential ingredient);

fermenting the carbon source substrate in an optimal condition established by feeding a substrate-base mixture of a carbon source substrate and at least one base selected from ammonium bicarbonate, sodium bicarbonate, and potassium bicarbonate in a fed-batch manner to the culture medium to allow the culture medium to have a pH of 4.5 to 7; and recovering butyric acid from the culture medium, the butyric acid being produced with the fermentation of the carbon source substrate.

The butyric acid-producing microorganism strain may be a *Clostridium* sp., and may be selected from the group consisting of *C. tyrobutyricum, C. butyricum*, and *C. acetobutyricum*.

With reference to FIG. 1, an embodiment of the present invention is explained.

The present invention is configured to feed a neutralizing solution containing a carbon source substrate and a base (e g., ammonium bicarbonate) in a fed-batch manner from a feeding tank to a fermenter where a carbon source substrate is fermented in the presence of a microorganism to produce an organic acid.

The fermenter may be equipped with a pH control sensor and/or a gas meter.

The pH control sensor aims to establish an optimal pH for the growth of the organic acid-producing microorganism in the culture medium in the fermenter. Within the fermenter, typical ingredients necessary for microorganism growth, such as a nitrogen source, may exist along with the carbon source substrate. When the pH of the culture medium deviates from a predetermined range as fermentation proceeds, the system is designed to automatically feed a mixture of a carbon source substrate and a base (e.g., ammonium bicarbonate). pH values suitable for the growth of individual organic acid-producing microorganisms are known in the art. For instance, when butyric acid is produced, an optimal pH value for the growth of butyric acid-producing microorganism is in the range of 4.5 to 7.

Together with or separately from the pH control sensor, a gas meter may be installed in the fermenter to measure the generated amount and generation rate of gas in the fermenter. The generation rate of gas provides information on the feeding rate of the substrate-base mixture or the time to terminate the feeding.

As described above, the time at which the feeding of the substrate-base mixture is terminated may be readily determined in consideration of the gas generation rate and the fed amount of the mixture by a person having ordinary skill.

As a rule, fermentation is inhibited by its end product (product inhibition). As the fermentation is carried out, the activity of the microorganism strain is decreased by the organic acid product. Often, fermentation may stop even when the carbon source substrate is not fully consumed. In this case, the carbon source substrate is wasted. In the present invention, a weak base such as ammonium bicarbonate is used as a neutralizer to prevent the microorganism strain from being influenced by high pH. The base neutralizes an organic acid such as butyric acid, with the concomitant generation of carbon dioxide ($CO_2$) and hydrogen ($H_2$) gas. The generation rate of the gas may be utilized to monitor the activity of the microorganism strain, providing the information of a proper time until the carbon source substrate is supplied. In the present invention, therefore, fermentation can be performed with the complete consumption of the carbon source substrate. Accordingly, since the supply of a carbon source substrate can be stopped at a proper time point to avoid the loss of remaining carbon source substrate, the fermentation process can be effectively operated with the maintenance of optimal activity in the microorganism. After completion of the feeding of the carbon source substrate and the base, the pH of the fermenter can be adjusted in a method known in the art, for example, by feeding a pH adjusting agent, such as ammonia water, alkali metal hydroxide solution, alkaline earth metal hydroxide solution a mixture thereof, e. g. sodium hydroxide, calcium hydroxide, potassium hydroxide, etc. at a constant rate.

In addition, when the fed-batch culture method according to the present invention is applied to fermentation for organic acid production, the culture medium described in the present invention can be used, instead of an expensive culture medium for the seed cultivation of bacterial fermentation, in the last stage of the culture for a seed train, thus greatly improving the economy of fermentation. Conventional butyric acid fermentation employs an RCM (Reinforced Clostridial Medium) or a similar nutrient-rich medium for a seed culture to improve the efficiency of the main culture. However, this expensive seed culture medium is a cause of increasing the production cost, degrading the economy of fermentation. In contrast, the fed-batch cultivation according to the present invention allows the culture medium for the last seed train to be employed in the main culture without a decrease in the activity of the microorganisms.

A better understanding of the present invention may be obtained through the following examples which are set forth to illustrate, but are not to be construed as limiting the present invention.

EXAMPLES

Comparative Example 1

Batch Culture

Sugar cane liquid and minerals (sugar concentration 150~200 g/L, 30 L) were placed in a 50 L anaerobic fermenter that was purged with nitrogen. Under this anaerobic condition, *Clostridium tyrobutyricum* was inoculated in a volume of 1%~20% of the broth to which ammonia water was then added so as to adjust the pH to 6.0. As fermentation proceeded at 37° C., carbon dioxide ($CO_2$) and hydrogen ($H_2$) were generated, maintaining the anaerobic condition.

EXAMPLE 1

Fed-Batch Culture

In a 50 L anaerobic fermenter, the same microorganism as in Comparative Example 1 was inoculated into sugar cane liquid and minerals (sugar concentration 20~40 g/L, 10~15 L), and then cultured at 37° C. while feeding a mixture of ammonium bicarbonate and sugar cane liquid (ammonium bicarbonate 80~120 g/L, sugar concentration 200~300 g/L, 15~20 L) to maintain the broth at a pH of 6.0. The fed-batch cultivation started with a smaller volume of a culture medium, compared to the batch cultivation, but the final volume of each culture medium was identical. Alternatively, the final volume could be adjusted. With the progress of the fermentation, $CO_2$ and $H_2$ gases were generated. When the generation rate of the gas was monitored to reach 1.5~2.5 L/L of fermenter/hr, the feeding of the mixture of ammonium bicarbonate and sugar cane liquid was terminated so that the fermentation proceeded until the sugar, fed up until that point, was completely consumed.

Both the cultivation methods of Comparative Example 1 and Example 1 produced butyric acid at a concentration of 6% or higher. For comparison, the two methods were examined for efficiency at the time point when the same concentration of butyric acid was achieved. Measurements of cell concentration ($OD_{600-MAX}$), productivity of butyric acid ($P_{BA}$), production yield of butyric acid ($Y_{BA}$), and production yield of acetic acid ($Y_{AA}$) for Comparative Example 1 (batch culture) and Example 1 (fed-batch culture) are given in Table 1, below.

TABLE 1

|  | $OD_{600-MAX}$ | $P_{BA}$ (g/L/hr) | $Y_{BA}$ (g BA/g sugar) | $Y_{AA}$ (g AA/g sugar) |
|---|---|---|---|---|
| Comparative example 1 | 56.6 | 1.31 | 0.376 | 0.051 |
| example 1 | 59 | 1.4 | 0.454 | 0.004 |

As is understood from data of Table 1, the fed-batch cultivation was superior in all indices to the batch cultivation. Particularly, the production of the by-product acetic acid (AA) was greatly inhibited in Example 1, with the consequent significant improvement of butyric acid in production yield. This increase in fermentation performance is understood to result from the maintenance of sugar at such a concentration as not to inhibit the growth of the microorganism. In contrast, the batch cultivation of Comparative Example 1 could not further ferment the sugar even when it maintained the initial concentration because the microorganism state differed from one batch to another. As a result, the sugar was not consumed completely, but remained In the fed-batch culture, the sugar could be completely consumed without loss because the time to stop supplying sugar could be controlled under the monitoring of the $CO_2$ and $H_2$ gas generation according to fermentation progress. The production yield of butyric acid (BA) according to the present invention was greatly increased, compared to the conventional batch culture or the stepwise addition of sugar in aliquots (refer to Comparative Example 2, below), demonstrating that the feeding of the sugar in mixture with ammonium bicarbonate for adjusting pH is highly reliable and efficient.

Example 2

Fed-Batch Culture by Feeding Mixture of Ammonium Bicarbonate and Medium

In this Example, fed-batch culture was demonstrated to greatly improve the concentration butyric acid (BA). Because BA itself is toxic to the microorganism that produces BA, it inhibits the activity of the microorganism (product inhibition), which results in no further production of the product even when the substrate sugar is present. Accordingly, the production yield of the acid is limited or the sugar is wasted. This Example was designed to maintain the activity of microorganism by controlling a proper concentration of sugar to minimize an osmotic change on the microorganism, thereby producing BA at a high concentration.

In this Example, a bioreactor system composed of a feeding tank and a fermenter was employed. In the fermenter, fermentation started with a culture medium having a volume of 20%~50% of a desired final volume while the remaining volume was fed at a rate depending on pH change from the feeding tank filled with a substrate-base mixture (a pH adjusting agent containing a carbon source substrate and a base).

The culture medium of the fermenter had the following composition: 14 L of a solution of sugar cane syrup 0.8 L, organic nitrogen source CSP(Corn Steep Powder) 180 g, and $FeSO_4 \cdot 7H_2O$ 1.8 g in water was added with 1.5 ml of an antifoaming agent, and autoclaved to give a medium. Separately, 1 L of an aqueous solution containing 54 g of $KH_2PO_4$ was autoclaved and completely cooled. This was fed, together with the medium, into the fermenter. For a medium reservoir in the feeding tank, 19.5 L of an aqueous solution containing 7.4 L of sugar cane syrup was mixed with 2 ml of an antifoaming agent. After autoclaving, the solution was added with 2 kg of ammonium bicarbonate ($NH_4HCO_3$), introduced into the feeding tank, and stirred for 12 hrs to completely dissolve ammonium bicarbonate.

A seed culture of *Clostridium tyrobutyricum* was inoculated in an amount of 3 L into the fermenter. Optionally, an enzyme (invertase) was added at a concentration of several ppm.

Immediately after the inoculation, the pH of the culture medium was adjusted to 6.3 with ammonia water. Fermentation was carried out in the following condition: pH : 6.3, Temp.: 37° C., stiffing speed: 200 rpm.

While the fermentation proceeded, a suitable amount of CSP might be additionally introduced into the fermenter. When the gas generation rate was monitored to reach 1.5~2.5 L/L of fermenter/hr, the feeding was stopped. Since then, the pH of the medium was adjusted with ammonia water until the fermentation was completed.

Comparative Example 2

For comparison with Example 2, fermentation was performed in a batch manner The culture medium of the fermenter had the following composition: 27 L of a solution of sugar cane syrup 8 L, organic nitrogen source CSP(Corn Steep Powder) 330 g, and $FeSO_4 \cdot 7H_2O$ 1.6 g in water was added with 3 ml of an antifoaming agent, and autoclaved to give a medium. Separately, 1 L of an aqueous solution containing 49 g of $KH_2PO_4$ was autoclaved and completely cooled. This was fed, together with the medium, into the fermenter. After autoclaving, a seed culture of *Clostridium tyrobutyricum* was inoculated in an amount of 3 L into the fermenter. Optionally, an enzyme (invertase) was added at a concentration of several ppm.

Immediately after the inoculation, the pH of the culture medium was adjusted to 6.3 with ammonia water. Fermentation was carried out in the following condition: pH : 6.3, Temp. : 37° C., stiffing speed: 200rpm.

Figure 2:
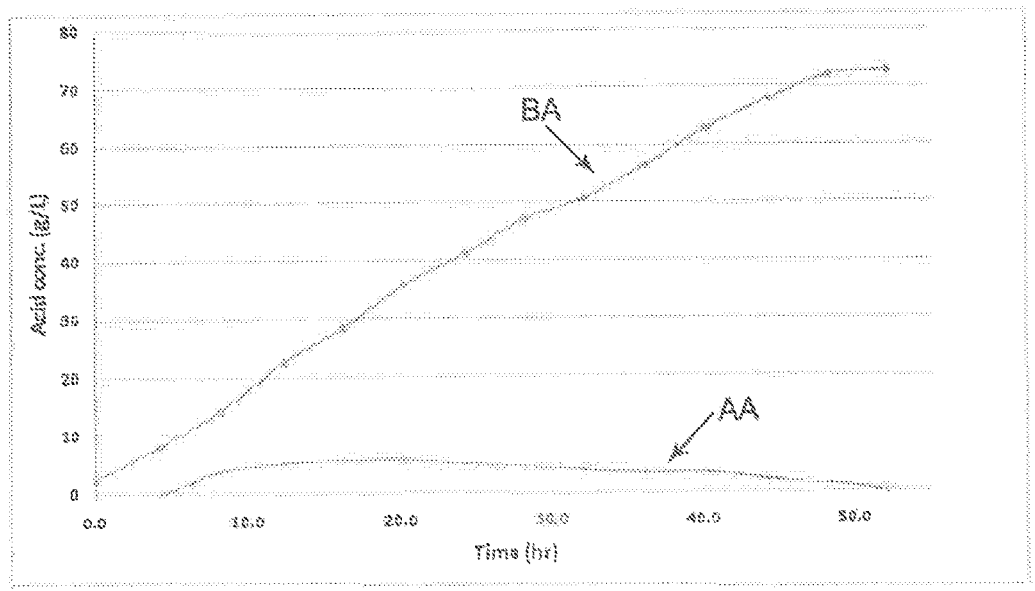
FIG. 2 shows production profiles of the product butyric acid and the by-product acetic acid.

Fermentation results of Example 2 and Comparative Example 2 are summarized in Table 2, below. It can be understood from the data of Table 2 that the fed-batch culture according to the present invention (Example 2) greatly improved in all indices accounting for fermentation performance and BA titer, compared to the conventional batch culture (Comparative Example 2). FIG. 2 shows production profiles of the product BA and the by-product acetic acid (AA). As can be seen, a decrease in AA production was detected in the fed-batch culture, making contribution to an improvement in fermentation yield and BA productivity.

TABLE 2

|  | BA Titer (g/L) | AA Titer (g/L) | BA Yield (g/g sugar) | BA Productivity (g/L/hr) |
| --- | --- | --- | --- | --- |
| Fed-batch culture | 72.8 | 0 | 0.465 | 1.37 |
| Batch culture | 63.9 | 9.58 | 0.386 | 1.301 |

Comparative Example 3

In this Comparative Example, sugar was fed in an intermittent manner, together with various bases, so as to confirm the effect of the fed-batch culture on the production of organic acids. The initial pH of the fermenter prior to the initiation of fermentation was adjusted with ammonia water to establish an environment proper for an organic acid-producing strain. After fermentation started, the base solutions listed in Table 3, below, were automatically added under monitoring with a pH probe while a solution composed solely of sugar was intermittently fed. The intermittent introduction of sugar was carried out in such a way that sugar was fed at regular time intervals or on the basis of analysis sugar data continuously measured, as shown in Table 3.

Sugar cane liquid, an organic nitrogen ingredient (RCM: Reinforced Clostridial Medium), and minerals (sugar concentration 30~100 g/L, 30 L) were placed in a 50 L anaerobic fermenter that was purged with nitrogen. Under this anaerobic condition, *Clostridium tyrobutyricum* was inoculated in a volume of 1%~20% of the broth to which ammonia water was then added so as to adjust the pH to 6.0. As fermentation proceeded at 37° C., carbon dioxide ($CO_2$) and hydrogen ($H_2$) were generated, maintaining the anaerobic condition.

Table 3 summarizes data of the final concentration, productivity, production yield and selectivity of butyric acid (BA) produced under the fermentation condition after the fermentation Fed-batch #1: A total amount of sugar required for the overall fermentation was fed in three equal aliquots when the sugar concentration measured 1~10 g/L. As a base, a dilution of ammonia was used in an amount shown in Table 3.

Fed-batch #2: A total amount of sugar required for the overall fermentation was fed in six equal aliquots when the sugar concentration measured 20 g/L. Thus, the total concentration of sugar was maintained at 20~40 g/L. As a base, a dilution of ammonia was used in an amount shown in Table 3.

Fed-batch #3: A total amount of sugar required for the overall fermentation was fed in to three equal aliquots when the sugar concentration measured 1~10 g/L. This was the same as in #1, but the base was changed from ammonia to $Ca(OH)_2$ to examine the effect of bases change.

Fed-batch #4: A total amount of sugar required for the overall fermentation was continually fed in multiple portions (10 times) to maintain a sugar concentration of 30 g/L. This was similar to the condition of #2, but the frequency of feeding was more so that the sugar concentration fluctuated to a less extent during the fermentation.

TABLE 3

|  | Medium (base) | Final Conc. (%) | Producti-vity (g/L · hr) | Yield (g/g) | Selecti-vity (%) | Note[1] |
| --- | --- | --- | --- | --- | --- | --- |
| Fed-Batch #1 | RCM (ammonia: 7-7.5%, 4.9 L) | 3.5 | 0.36 | 0.32 | 84 | Acetate 0.67% Lactate 0% |
| Fed-Batch #2 | RCM (ammonia: 7-7.5%, 4.9 L) | 3.4 | 0.68 | 0.34 | 60 | Lactate 1.3% Acetate 1% |
| Fed-Batch #3 | RCM ($Ca(OH)_2$; 20% 2.2 L) | 3.0 | 0.27 | 0.33 | 88 | Acetate 0.42% Lactate 0% |
| Fed-Batch #4 | RCM (ammonia: 7-7.5%, 4.9 L) | 3.5 | 0.35 | 0.33 | 78 | Acetate 1.01% Lactate 0% |

[1] Concentrations of different organic acids other than BA of the product (%)

As shown in Table 3, there was no strategy that predominated over the other strategies in terms of productivity, production concentration, and yield. For example, fed batch #2 was observed to increase in productivity, but decrease in selectivity.

In addition, the intermittent sugar feeding strategy is difficult to apply to practical processes not only because it is highly prone to failing in controlling a proper sugar concentration, but because it is labor intensive, and is likely to cause difficulty in automation and is prone to contamination due to frequent analysis.

The invention claimed is:

1. A method for producing an organic acid by fed-batch culture, comprising:
   (i) preparing a culture medium containing a carbon source substrate, an organic acid-producing strain of bacteria, and a growth ingredient for said strain of bacteria;
   (ii) fermenting said culture medium to produce said organic acid;
   (iii) measuring a pH change in said culture medium;
   (iv) correlating said pH change to consumption of said carbon source substrate;
   (v) fed-batch feeding additional substrate-base mixture of carbon source substrate and an alkali metal containing weak base to said culture medium in an amount to maintain concentration of said carbon source substrate, and said alkali metal containing weak base in an amount to matain optimal pH for growth of said strain of bacteria, and (vi) removing any organic acid produced in said culture medium;

wherein ratio of carbon source substrate to alkali metal containing weak base is 200~300 g/L to 80~120 g/L, wherein $CO_2$ and $H_2$ gases are generated during said fermenting, and when $CO_2$ and $H_2$ gases reach a generation rate of 1.5-2.5 L/L of fermenter/hr, terminating the feeding the substrate-base mixture so that said fermenting proceeds until said carbon source substrate is completely consumed.

2. The method of claim 1, wherein, after completion of the feeding of the substrate-base mixture, ammonia water, alkali metal hydroxide solution, alkaline earth metal hydroxide solution, or a combination thereof is supplied to said fermenter to allow the culture medium to have a pH value optimal for growth of the organic acid-producing strain until the carbon source substrate is completely fermented.

3. The method of claim 1, wherein the growth ingredient is at least one selected from the group consisting of a nitrogen source, a vitamin, a mineral, and a carbon source degrading enzyme.

4. A method for producing butyric acid by fed-batch culture, comprising;

(i) preparing a culture medium containing a carbon source substrate, a butyric acid-producing strain of bacteria, and a growth ingredient for the strain of bacteria;

(ii) fermenting said culture medium to produce said butyric acid;

(iii) measuring a pH change in said culture medium;

(iv) correlating said pH change to consumption of said carbon source substrate;

(v) fed-batch feeding additional substrate-base mixture of carbon source substrate and at least one base selected from the group consisting of ammonium bicarbonate, sodium bicarbonate, potassium bicarbonate, ammonium carbonate, sodium carbonate, potassium carbonate and mixture thereof, in an amount to matain a pH of said culture medium to have a pH of 4.5 to 7; and (vi) removing any butyric acid produced in said culture medium;

wherein ratio of carbon source substrate to said at least one base is 200~300 g/L to 80~120 g/L, wherein $CO_2$ and $H_2$ gases are generated during said fermenting, and when $CO_2$ and $H_2$ gases reach a generation rate of 1.5-2.5 L/L of fermenter/hr, terminating feeding said substrate-base mixture so that said fermenting proceeds until the carbon source substrate is completely consumed.

5. The method of claim 4, wherein said butyric acid-producing strain of bacteria is a *Clostridium* sp. microorganism.

6. The method of claim 1, wherein said carbon source substrate is selected from the group consisting of glucose, fructose, sucrose, galactose, xylose, arabinose, sugar cane, molasses, and starch hydrolysate.

7. The method of claim 1, wherein the organic acid is at least one selected from the group consisting of butyric acid, lactic acid, acetic acid, formic acid, citric acid, adipic acid, succinic, acid, fumaric acid, malic acid, 3-hydroxypropionic acid, glutamic acid, glutaric acid, glucaric acid, itaconic acid, acrylic acid, and muconic acid.

8. The method of claim 1, wherein the organic acid-producing strain is selected from the group consisting of *Clostridium* spp., *Pseudomonas* spp., *Rhizopus* spp., *Aspergillus* spp., *Corynebacterium* spp., *Actinobacillus* spp., yeast, *Candida* yeast, *Pichia* yeast, *E. coli*, and lactic acid producing bacteria.

9. The method of claim 1, comprising fermenting said culture medium in a fermenter equipped with a pH control sensor, a gas meter or both.

* * * * *